United States Patent [19]

Willis

[11] Patent Number: 4,647,756

[45] Date of Patent: Mar. 3, 1987

[54] ELECTRICAL RESISTANCE HEATING ELEMENT WITH SIGNAL MEANS TO INDICATE FIRST USE

[75] Inventor: Frank M. Willis, Wenonah, N.J.

[73] Assignee: E. I. Du Pont de Nemours and Company, Wilmington, Del.

[21] Appl. No.: 511,017

[22] Filed: Jul. 5, 1983

[51] Int. Cl.[4] .................. B29C 27/06; H05B 3/10; B26D 7/10

[52] U.S. Cl. .................. 219/243; 156/159; 156/583.1; 219/221; 219/240; 219/506; 219/517; 337/1; 604/111

[58] Field of Search .............. 219/243, 253, 506, 517, 219/543, 528, 535, 221, 240; 337/4, 17, 409, 1; 128/11, 213 A, 303.1; 156/159, 583.1; 315/75, 111; 604/110, 111

[56] References Cited

U.S. PATENT DOCUMENTS

| | | | |
|---|---|---|---|
| 411,380 | 9/1889 | Heller | 337/17 |
| 426,024 | 4/1890 | Kammer | 337/17 |
| 1,203,125 | 10/1916 | Nuckols | 219/517 |
| 1,549,984 | 8/1925 | Hynes | 219/517 X |
| 1,803,486 | 5/1931 | Rau, Jr. | 315/75 |
| 2,159,649 | 5/1939 | Alford | 337/4 X |
| 2,874,248 | 9/1956 | Tondat et al. | 200/125 |
| 3,182,153 | 5/1965 | Postal | 219/543 |
| 3,249,800 | 5/1966 | Huber | 315/111 |
| 3,423,567 | 1/1969 | Mills | 219/517 X |
| 3,423,574 | 1/1969 | Shomphs et al. | 219/528 |
| 3,693,048 | 9/1972 | Doversberger et al. | 337/4 X |
| 3,924,099 | 12/1975 | Hausel | 219/517 X |
| 4,044,224 | 8/1977 | Jenkins et al. | 219/517 X |
| 4,169,254 | 9/1979 | Kennedy et al. | 337/409 |
| 4,342,977 | 8/1982 | McGalliard | 337/4 |
| 4,369,779 | 1/1983 | Spencer | 128/213 A |
| 4,406,280 | 9/1983 | Upsher | 128/11 |
| 4,479,105 | 10/1984 | Banes | 337/4 |
| 4,493,985 | 1/1985 | Keller | 219/535 |
| 4,501,951 | 2/1985 | Benin et al. | 219/243 |

FOREIGN PATENT DOCUMENTS 0049773 9/1981 European Pat. Off. ............ 219/517

Primary Examiner—Anthony Bartis

[57] ABSTRACT

The electric heating element in an apparatus for sterilely cutting and welding together a pair of thermoplastic tubes incorporates within the heating element a fusible signal means connected in parallel electrical circuit with the resistor of the heating element for indicating previous use of the heating element. The fusible signal means is capable when intact of providing a signal to a microprocessor controlling operation of the apparatus indicative of previous nonuse of the heating element and is automatically destructed upon energization of the heating element resistor during the first use of the heating element so as to be incapable of providing such nonuse signal upon a subsequent energization. If the nonuse signal is not generated, e.g., the heating element has been previously used, the microprocessor is programmed to reject the heating element, thereby eliminating risks resulting from reusing the heating element.

19 Claims, 5 Drawing Figures

ELECTRICAL RESISTANCE HEATING ELEMENT WITH SIGNAL MEANS TO INDICATE FIRST USE

BACKGROUND OF THE INVENTION

This invention relates to a printed circuit heating element. More specifically, the present invention relates to a printed circuit heating element suitable for heating and welding two thermoplastic tubes together.

At the present time there are a number of medical and scientific procedures which require the sterile transfer of fluids from one container to another. An example of the need for sterile docking is in continuous ambulatory peritoneal dialysis (CAPD). The CAPD patient has a tube connected to his or her peritoneal cavity via an implanted catheter. A tube from a bag of fresh dialysis solution is connected to the patient's tube. The fresh dialysis solution is drained from the bag into the patient's peritoneal cavity where it remains for about 3–4 hrs. After this treatment period, the spent dialysate is drained back into the empty bag which is then disconnected from the patient's tube. A bag of fresh dialysis solution is then connected to the patient's tube and the procedure repeated. A similar need for sterile connection exists for blood bags.

U.S. Pat. No. 4,369,779, issued to Spencer on Jan. 25, 1983, discloses an apparatus and process for forming a sterile connection. The apparatus comprises a cutting means, means adapted to heat said cutting means, a pair of mounting blocks adapted to receive and hold two tubes to be joined, means to provide movement between said blocks and said cutting means to a position such that the cutting means is between said blocks and traversing where the blocks are adapted to receive tubes, means adapted to realign said blocks to a position where two different tube ends are aligned with and facing each other, and means to separate said blocks and said cutting means while urging said blocks together. The patent discloses that the cutting means can take many forms but preferably is a laminate strip constructed of an etched stainless steel ribbon having on each side an acrylic adhesive layer, an aromatic polyimide layer, an acrylic adhesive layer and a copper ribbon.

U.S. Pat. No. 4,501,951 discloses a heating element for use in the aforesaid apparatus for sterile connection consisting essentially of, as an outside layer, a folded sheet of metal having a thermal conductivity of at least about 173 watts/m°K. at a 0.10 mm thickness and a tensile yield strength of at least about $34 \times 10^4$ kPa at a 0.10 mm thickness, a resistor disposed inside the fold of said folded sheet of metal; and a layer of dielectric adhesive, stable to about 260° C., between inner surfaces of said folded sheet of metal and surfaces of said resistor, thereby bonding the resulting structure together. The application further discloses that preferably the resistor is an etched foil resistor made from stainless steel.

Resistance heating elements for use in the aforesaid sterile connection apparatus can be reused if properly cleaned and if they are still structurally intact. However, improper cleaning may result in a joint of low strength and in contamination of the insides of the tubes which are welded together. Moreover, the number of times a heating element can be reused depends upon the particular element. Furthermore, the determination of whether a heating element has been properly cleaned or is structurally intact cannot be easily done by the ordinary user. Uncertainties such as these, subject the patient who is using the device to unnecessary risks of infection. A means by which these risks may be minimized, eliminated or avoided would prove advantageous.

Fuses which melt to deactivate or bypass a circuit are well known. U.S. Pat. No. 411,380 issued to Heller and U.S. Pat. No. 1,803,486 issued to Rau are typical of patents disclosing fusible elements to bypass an incandescent electric lamp. U.S. Pat. No. 2,874,248, issued to Tondat et al. on Feb. 17, 1959, discloses a multiple fuse assembly having a movable bridging contactor to engage one fuse at a time. The patent discloses that the assembly may be produced by printed circuit technology or by spraying a paint containing powdered metal through a suitable mask to produce the desired outline on an insulating board, and then drying and baking the resulting coating.

U.S. Pat. No. 3,249,800, issued to Huber on May 3, 1966, discloses a fast acting switch wherein a small metal wire is exploded electrically and rapidly to pulse a circuit by electrically disintegrating the wire explosively to form a rapidly expanding, current carrying, low impedance conducting medium in the gap between two closely spaced conductors so as to actuate and conduct the flow of current between the conductors.

U.S. Pat. No. 4,169,254, issued to Kennedy et al. on Sept. 25, 1979, discloses a manually actuable electric switch having a fusible element which melts on subjection to a predetermined temperature to discontinue the flow of electric current through the switch. A manually operable plunger normally used to open and close the switch is mechanically connected to the stem of the switch through the fusible element. Melting of the element severs the mechanical connection between the plunger and switch thereby deactivating the switch.

SUMMARY OF THE INVENTION

The present invention provides an improvement in a resistance heating element for welding thermoplastic tubes together. The improvement comprises a fusible signal means to indicate first use of the element, said signal means being connected in parallel to the resistor of said heating element and providing an electrical signal which is eliminated during first use of said heating element. The resistance heating element includes an electrical resistor for producing heat when connected in circuit with a power supply. The fusible signal means is capable when intact of providing a signal indicative of previous nonuse of the heating element and being automatically self-destructable upon energization of the heating element during the first use of the heating element so as to be incapable of providing the signal indicative of previous nonuse upon a subsequent energization of the heating element.

DETAILED DESCRIPTION OF THE INVENTION

Figure 1:
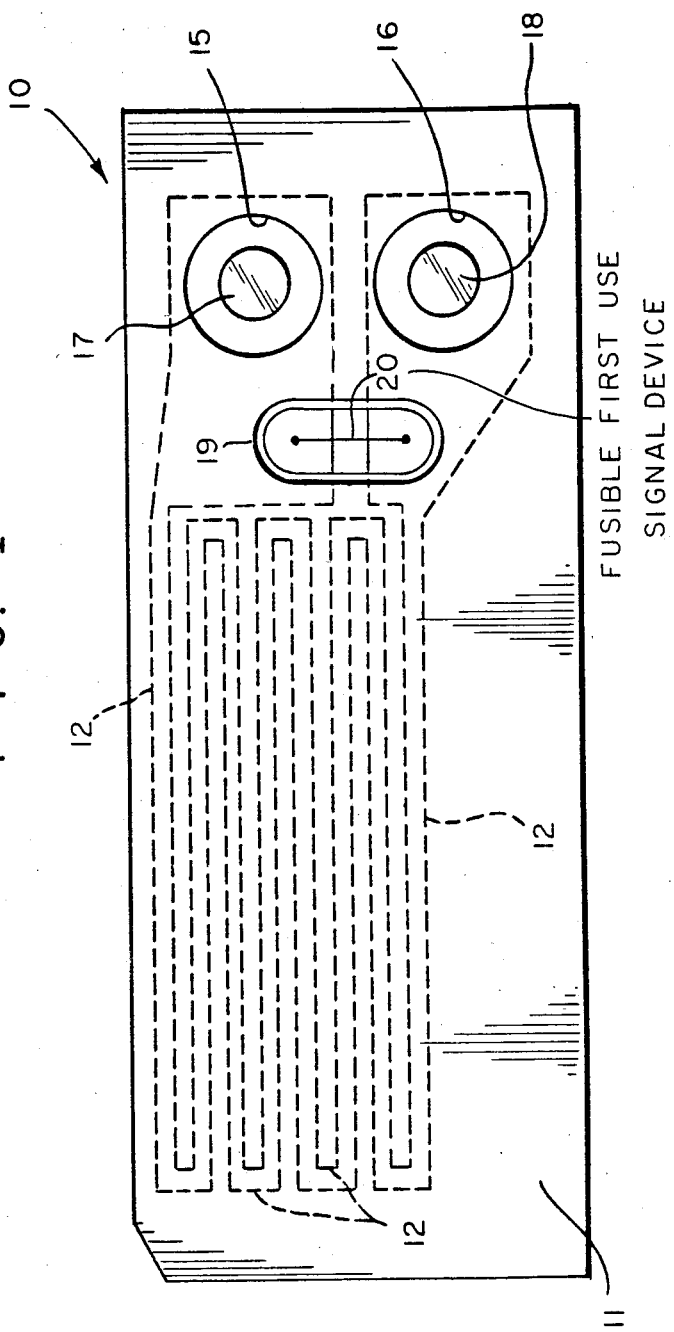
FIG. 1 is a plan view of a heating element having a fusible signal means in accordance with the present invention.

Referring to FIG. 1, heating element 10 is shown with resistor 12 which is made from etched stainless steel foil for this embodiment. Resistor 12 is disposed in the fold of a folded sheet 11 of metal which in the figure is copper and serves as the outer layer of the heating element. Openings 15 and 16 are provided on one side of folded sheet 11 thereby exposing terminals or contacts 17 and 18, respectively, of resistor 12. Opening 19 is also provided on one side of the folded sheet 11 to expose fusible signal means 20 which for the embodiment disclosed in the figure is a stainless steel wire. The fusible signal means can be connected in parallel to all or at least part of the resistor.

Figure 2:
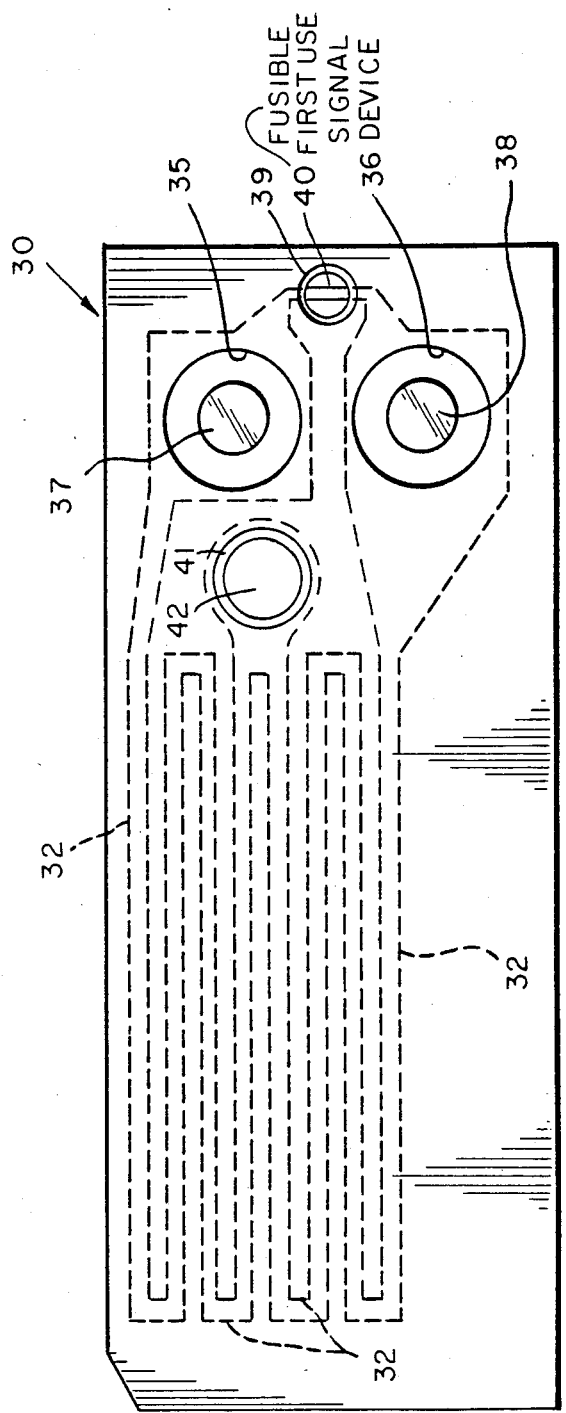
FIG. 2 is a plan view of a heating element having a fusible signal means in accordance with another embodiment of the present invention.

Referring now to FIG. 2, heating element 30 is shown with fusible signal means or element 40 which is made during etching of stainless steel resistor 32. Opening 39 provides exposure of element 40. Terminal 42 exposed by opening 41 affords quality control checking of the resistor. Checking between shorted terminals 37 and 38 and terminal 42 will form two parallel paths of equal resistance.

The fusible signal means can be a strip or wire made from a fusible elemental metal, metal alloy or other conductive material. The term "fusible" as used herein means that the strip or signal means becomes upon heating severed or separated by melting, vaporizing or oxidizing. Although the term "melt" will be used subsequently to exemplify how the fusible signal means becomes severed, it is to be understood that destruction by vaporization or oxidation equally applies. Preferably, the strip or wire is made from a fusible elemental metal or metal alloy. Suitable materials include steel, stainless steel, NICHROME resistance wire, copper, aluminum, zinc, tin, lead and alloys of any of these materials. Preferably, the fusible signal means is made from aluminum or stainless steel since these materials are commonly used in the art to make fusible links. The strip or wire can be made by appropriately dimensioning the width, thickness and length of the strip or diameter and length of the wire so that, within the desired circuit and within a repeatable heat-transfer environment, it will heat up rapidly to the melting point of the material used. The fusible signal means can also be made from a low melting point alloy, such as a eutectic alloy, which is not melted solely by the action of the current through it but rather by its close proximity to the heating element. In this embodiment, the melting point of the alloy must be below the temperature generated by the heating element.

In a preferred embodiment of the invention the resistance heating element has an etched stainless steel foil resistor and the fusible signal strip is made from stainless steel and is produced during etching of the resistor. Preferably, in this embodiment of the invention, the resistance heating element consists essentially of, as an outer layer, a folded sheet of metal having a thermal conductivity of at least about 173 watts/m°K. at a 0.10 mm thickness and a tensile yield strength of at least about $34 \times 10^4$ kPa at a 0.10 mm thickness, an etched stainless steel foil resistor disposed inside the fold of said folded sheet of metal; and a layer of dielectric adhesive, stable to about 260° C., between inner surfaces of said folded sheet of metal and surfaces of said resistor, thereby bonding the resulting structure together. This heating element is described in U.S. Pat. No. 4,501,951.

The fusible signal means can be welded or mechanically crimped onto the desired location, can be pressure bonded to a roughened surface of the contact pads of the heating element, or can be connected by other methods known in the art. For a repeatable operation where the critical measurement is a small change in heat-up time, the fuse heat-transfer environment should be maintained constant.

The improved heating element of the invention is used in the sterile connection apparatus described in U.S. Pat. No. 4,369,779. Preferably, the apparatus is equipped with a microprocessor capable of detecting the electrical signal generated by the fusible signal means. A suitable apparatus equipped with a microprocessor is described in U.S. patent application Ser. No. 408,418 filed on Aug. 16, 1982, now abandoned in favor of c-i-p application Ser. No. 637,581 filed on Aug. 3, 1984, now U.S. Pat. No. 4,521,263, issued June 4, 1985.

The improved resistance heating element of the invention when used in the sterile connection device as described in U.S. Pat. No. 4,369,779 provides an electrical signal to indicate whether or not the heating element is being used for the first time. The fusible signal means then melts instantly permitting heating of the heating element to proceed. If multiple use of a heating element is being attempted, the microprocessor of the sterile connection device would not receive the electrical signal of the fusible signal means and would then reject the blade by refusing to continue through its heating and splicing cycle. An audible signal could be generated to tell the patient that the sterile connection operation has not been commenced.

The presence of the fusible signal means can be determined by applying a low voltage to the heating element and then measuring the resistance. For instance, if the fusible signal means having a resistance of 2 ohms ($R_1$) was used in parallel with a 10 ohm ($R_2$) heating element resistor, the equivalent resistance, $R_{eq}$, of the circuit would be $$1/R_{eq} = 1/R_1 + 1/R_2 = 6/10$$

Hence, $R_{eq}$ is 1.67 ohms which is slightly less than the fusible signal means resistance. If the fusible signal means had been absent, the resistance would have been that of the heating element resistor, i.e., 10 ohms. This differential of 83% is easily detected. Even if the fuse resistance equalled the blade resistance, the differential would be 50% which is still easily detected.

Another and preferred method to detect the presence of the fusible signal means is to monitor the time it takes to reach the melt-voltage of the fusible signal means. A percent increase in time of about 200% between the absence and presence of the signal means can be obtained in the melt-voltage method. A third method for detecting the presence of the fusible signal means is to monitor the slope of the voltage/time curve for an inflection point where the signal means melts.

Figure 3:
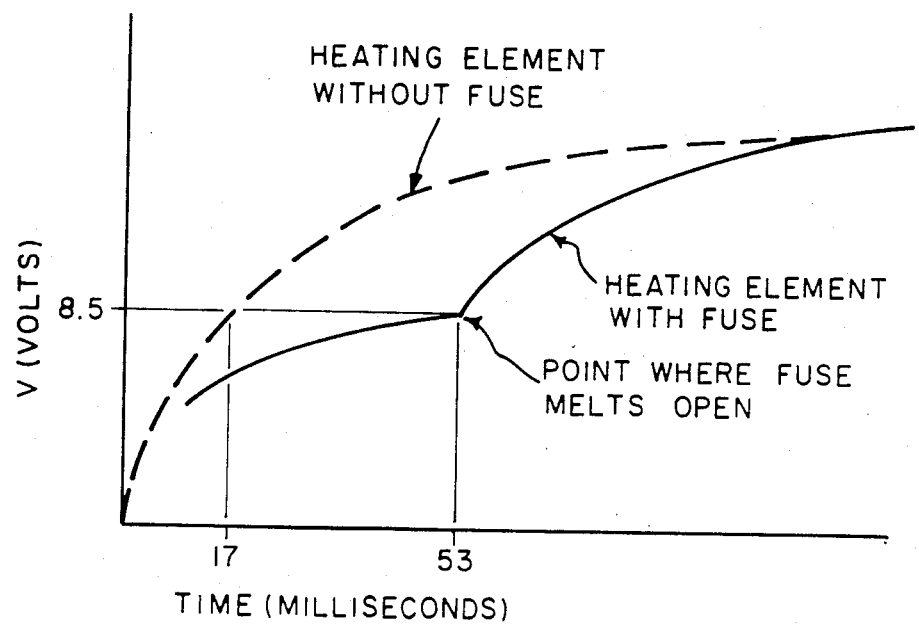
FIG. 3 is a graph depicting a voltage-time relationship for heating element of the invention.

A heating element constructed pursuant to U.S. Pat. No. 4,501,951 was selected for use in the sterile connection apparatus described in U.S. patent application Ser. No. 408,418 now abandoned in favor of c-i-p application Ser. No. 637,581 filed on Aug. 3, 1984, now U.S. Pat. No. 4,521,263, issued June 4, 1985. The element had an outer layer made of rolled, annealed copper with a thickness of 0.11 mm, an etched stainless steel resistor with a thickness of about 0.025 mm, a layer of acrylic adhesive 0.025 mm in thickness. A stainless steel wire having a diameter of 0.04 mm (1.6 mil), a length of 1.3 cm (0.5 inch) and a resistance of about 3 ohms was connected in parallel between the terminals of the resistor. The particular sterile connection apparatus used employs a 1.35 amp current for heating. When this current was applied to the heating element, the voltage/time relationship shown in FIG. 3 resulted. As can be seen from FIG. 3, the time to reach a preselected voltage, the fuse-melt voltage, was considerably different with as compared to without a fuse. To reach a value of 8.5 volts it took 53 milliseconds with the steel wire as a fuse and only 17 milliseconds without it. This 36 millisecond difference can be readily detected with the microprocessor of the apparatus. If the heating elements are carefully quality controlled to assure that each will reach a desired voltage within a time period that retains significance for this difference between the presence and absence of the fuse, then the apparatus can be programmed to indicate when a heating element has reached the desired voltage too rapidly, thereby determining whether the fuse was absent and thus an attempted nonfirst use.

Figure 4:
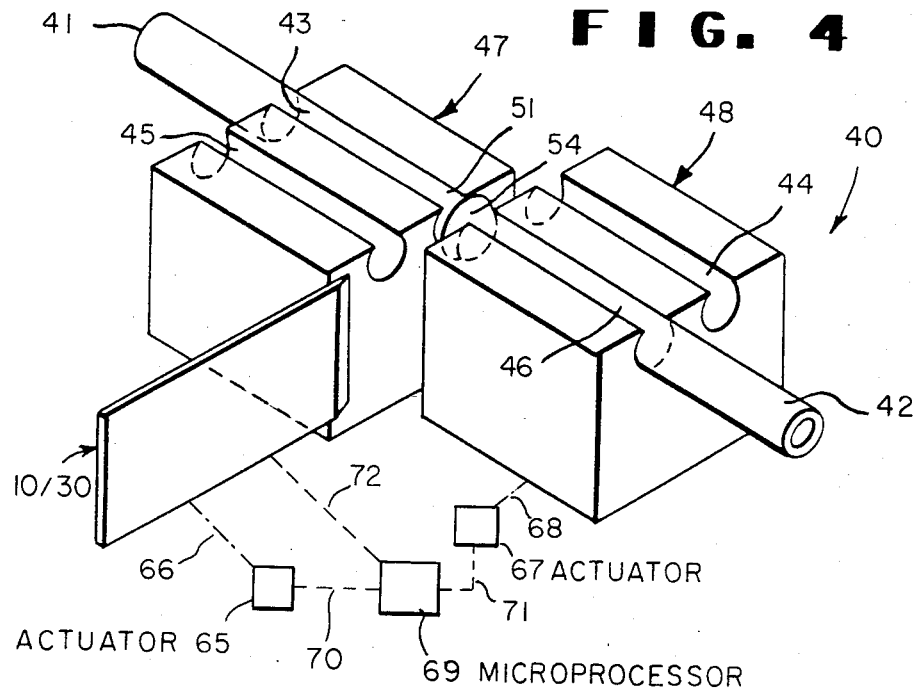
FIG. 4 is a perspective view of the mounting blocks, cutting means and welded tubes.
Figure 5:
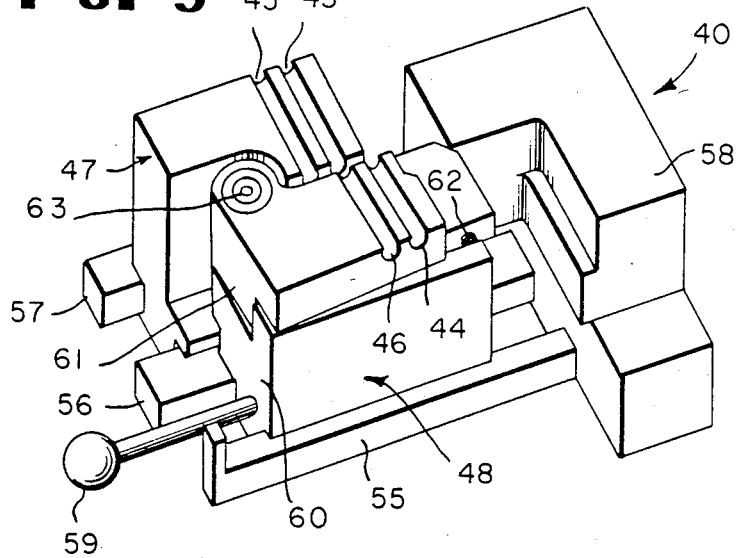
FIG. 5 is a perspective view of the mounting blocks slidably mounted on their guides.

Referring to FIGS. 4 and 5 an apparatus generally indicated by reference character 40 for forming a sterile connection between two thermoplastic tubes 41 and 42 is shown. The apparatus 40 includes a pair of mounting blocks 47 and 48. In FIG. 5 the block 48 is shown as comprised of two parts 60, 61 which are joined together by a bolt 63 so as to allow rotational motion of the part 61. As is also seen in FIG. 5 the blocks 47 and 48 are slidably mounted in guides 55, 56 and 57. A biasing spring 62 urges the upper part 61 of the block 48 toward the block 47. The block 47 as slots 43 and 45 formed therein, while the upper part of the block 48 is provided with corresponding slots 44 and 46, respectively.

In operation, the blocks are originally positioned with the axes of the slots 43 and 44 and those of the slots 45 and 46 being coaxial and arranged such that the tube 41 is received in the slots 43, 44 and the tube 42 is received in the slots 45 and 46. A cutting means in the form of a cutting element 10/30 as shown in FIGS. 1 and 2 is positioned between the blocks 47 and 48. An actuator 65 is operatively associated with the cutting element 10/30, as indicated by the schematic connection 67. The actuator 65 is operative to cause the cutting element 10/30 to move from a retracted position to a position where the cutting element traverses the place where the tubes 41, 42 pass from the slots on one block to the slots on the other block thereby to cut through both of the tubes 41 and 42. A suitable actuator 67 is operatively associated with the block 48, as indicated by the schematic connection 68. The actuator 67 serves to displace the block 48 from the original position to a second position in which the axis of the portion of the tube 41 in the slot 43 is aligned with the axis of the portion of the tube in the slot 46. This position is illustrated in FIG. 4. The cutting element 10/30 is then withdrawn and the molten interfaces 51 and 54 on the aligned portions of the tubes are urged toward each other by the action of the spring 62. The resulting joint exhibits a slight compression, as seen in FIG. 4. The motion of the block may be imparted manually, as by an operating handle 59. The travel of the block 48 is limited by a stop block 58.

A microprocessor 69 is connected to both of the actuators 65 and 66 as well as to the fusible signal means provided in the cutting element 10/30, as illustrated by the respective connections 70, 71 and 72. As earlier discussed, the fusible signal means provides an electrical signal which is detectable by the microprocessor 69 indicative of previous nonuse of the cutting element 10/30 and which is eliminated during the first use of the heating element so as to be incapable of providing the signal upon subsequent energization of the heating element.

The foregoing is considered illustrative only of the principles of the invention. Various modifications and changes may be made without departing from the spirit and scope of the invention.

The invention being claimed is:

1. In an electric resistance heating element for welding thermoplastic tubes together, said heating element including an electrical resistor for producing heat when connected in circuit with a power supply, the improvement comprising, in combination with said heating element's resistor, a fusible signal means incorporated within said heating element, said fusible signal means being connected in parallel electrical circuit with the resistor of said heating element, said fusible signal means being capable when intact of providing a signal indicative of previous nonuse of said heating element and being automatically self-destructable upon energization of said heating element resistor during the first use of said heating element so as to be incapable of providing the signal indicative of previous nonuse upon a subsequent energization of said heating element resistor.

2. A resistance heating element according to claim 1 wherein the fusible signal means is formed from a of fusible conductive material.

3. A resistance heating element according to claim 2 wherein the fusible signal means is a fusible metal.

4. A resistance heating element according to claim 3 wherein the fusible metal is aluminum.

5. A resistance heating element according to claim 2 wherein the fusible signal means is a wire.

6. A resistance heating element according to claim 2 wherein the fusible signal means is a strip of alloy.

7. A resistance heating element according to claim 6 wherein the alloy is stainless steel.

8. A resistance heating element according to claim 7 wherein the heating element has an etched stainless steel foil resistor and the fusible signal strip of stainless steel is made during etching of the resistor.

9. A resistance heating element according to claim 6 wherein the alloy is low melting.

10. In an electrical heating element for welding first and second thermoplastic tubes together transversely of the axis of each tube, said heating element consisting essentially of, as an outer layer, a folded sheet of metal having a thermal conductivity of at least about 173 watts/m°K. at a 0.10 mm thickness and a tensile yield strength of at least about $34 \times 10^4$ kPa at 0.10 mm thickness, an electrical resistor comprising an etched stainless steel foil disposed inside the fold of said folded sheet of metal; and a layer of dielectric adhesive, stable to about 260° C., between inner surfaces of said folded sheet of metal and surfaces of said resistor, thereby bonding the resulting structure together, the improvement comprising an etched fusible signal strip of stainless steel connected in parallel electrical circuit with the resistor, said fusible signal strip being disposed within the fold of said folded sheet of metal so as to be incorporated within the heating element, said fusible signal means being capable when intact of providing a signal indicative of previous nonuse of said heating element and being automatically self-destructable upon energization of said heating element resistor during first use of the heating element so as to be incapable of providing the signal indicative of previous nonuse upon a subsequent energization of said heating element resistor, said fusible signal strip being made during etching of the resistor.

11. In an apparatus for forming a sterile connection between two thermoplastic tubes, which apparatus comprises a cutting means, a pair of mounting blocks adapted to receive and hold the two tubes, means to provide movement between said blocks and said cutting means to a position such that the cutting means is between said blocks and traversing where the blocks are adapted to receive tubes, means adapted to realign said blocks to a position where two different tube ends are aligned with and facing each other, means to separate said blocks and cutting means while urging said blocks together; and a microprocessor to control the means to provide movement between blocks and cutting means; the improvement comprising the cutting means having an electrical resistance heating element with a fusible signal means incorporated therein to indicate first use of the element, said fusible signal means being connected in parallel electrical circuit with the resistor of said heating element, said fusible signal means being capable when intact of providing a signal to the microprocessor indicative of previous nonuse of said heating element and being automatically self-destructable upon energization of said heating element resistor during first use of the heating element so as to be incapable of providing the signal indicative of previous nonuse upon a subsequent energization of said heating element resistor.

12. In an apparatus according to claim 11, the improvement wherein the fusible signal means is formed from a fusible conductive material.

13. In an apparatus according to claim 12, the improvement further comprising that the fusible signal means is a strip of fusible metal.

14. In an apparatus according to claim 13, the improvement further comprising that the fusible metal is aluminum.

15. In an apparatus according to claim 12, the improvement further comprising that the fusible signal means is a strip of alloy.

16. In an apparatus according to claim 15, the improvement further comprising that the alloy is low melting.

17. In an apparatus according to claim 15, the improvement further comprising that the alloy is stainless steel.

18. In an apparatus according to claim 17, wherein the heating element has an etched stainless steel foil resistor, the improvement further comprising that the fusible signal strip of stainless steel is an etched strip made during etching of the resistor.

19. In an apparatus according to claim 11, the improvement further comprising that the fusible signal means is a stainless steel wire connected between contacts of said heating element, said wire having a diameter of about 0.038 mm and a length of at least about 2 mm.

* * * * *